United States Patent [19]
Sage et al.

[11] Patent Number: 5,265,628
[45] Date of Patent: Nov. 30, 1993

[54] AUTOMATED CLEANSING CHAMBER

[75] Inventors: Howard Sage, Phoenix, Ariz.; David Newton, Boulder, Colo.; Gary Cooper, Englewood, Colo.; Donald Berns; Christopher Maybach, both of Parker, Colo.

[73] Assignee: Meritech, Inc., Englewood, Colo.

[21] Appl. No.: 889,946

[22] Filed: Jun. 2, 1992

[51] Int. Cl.⁵ .................................................. B08B 3/02
[52] U.S. Cl. ................................. 134/58 R; 134/95.3; 134/103.3; 134/104.1; 134/181
[58] Field of Search ................. 134/65, 119, 120, 121, 134/153, 155, 172, 180, 181, 199, 200, 201, 104.1, 58 R, 95.3, 103.3; 604/289; 132/74.5; 4/621, 623; 422/28, 106, 292; 68/143, 144

[56] References Cited

U.S. PATENT DOCUMENTS

| | | | |
|---|---|---|---|
| 3,243,264 | 3/1966 | Hickey | 134/65 X |
| 3,699,984 | 10/1972 | Davis | 134/199 X |
| 3,754,559 | 8/1973 | Seiwert | 134/65 |
| 3,757,806 | 9/1973 | Bhaskar et al. | 134/199 X |
| 3,918,987 | 11/1975 | Kopfer | 134/199 X |
| 4,073,301 | 2/1978 | Mackinnon | 134/65 |
| 4,817,651 | 4/1989 | Crisp et al. | 134/199 X |
| 4,925,495 | 5/1990 | Crisp et al. | 134/561 R X |
| 4,942,631 | 7/1990 | Rosa | 4/623 |

Primary Examiner—Philip R. Coe
Attorney, Agent, or Firm—Rick Martin

[57] ABSTRACT

Rotating nozzles in a cylinder comprise a hand washing system that through a program provides purge, wash, dwell, rinse and self clean cycles. In ten seconds 99% of bacteria are killed without hand irritation even with multiple hand washes daily.

13 Claims, 18 Drawing Sheets

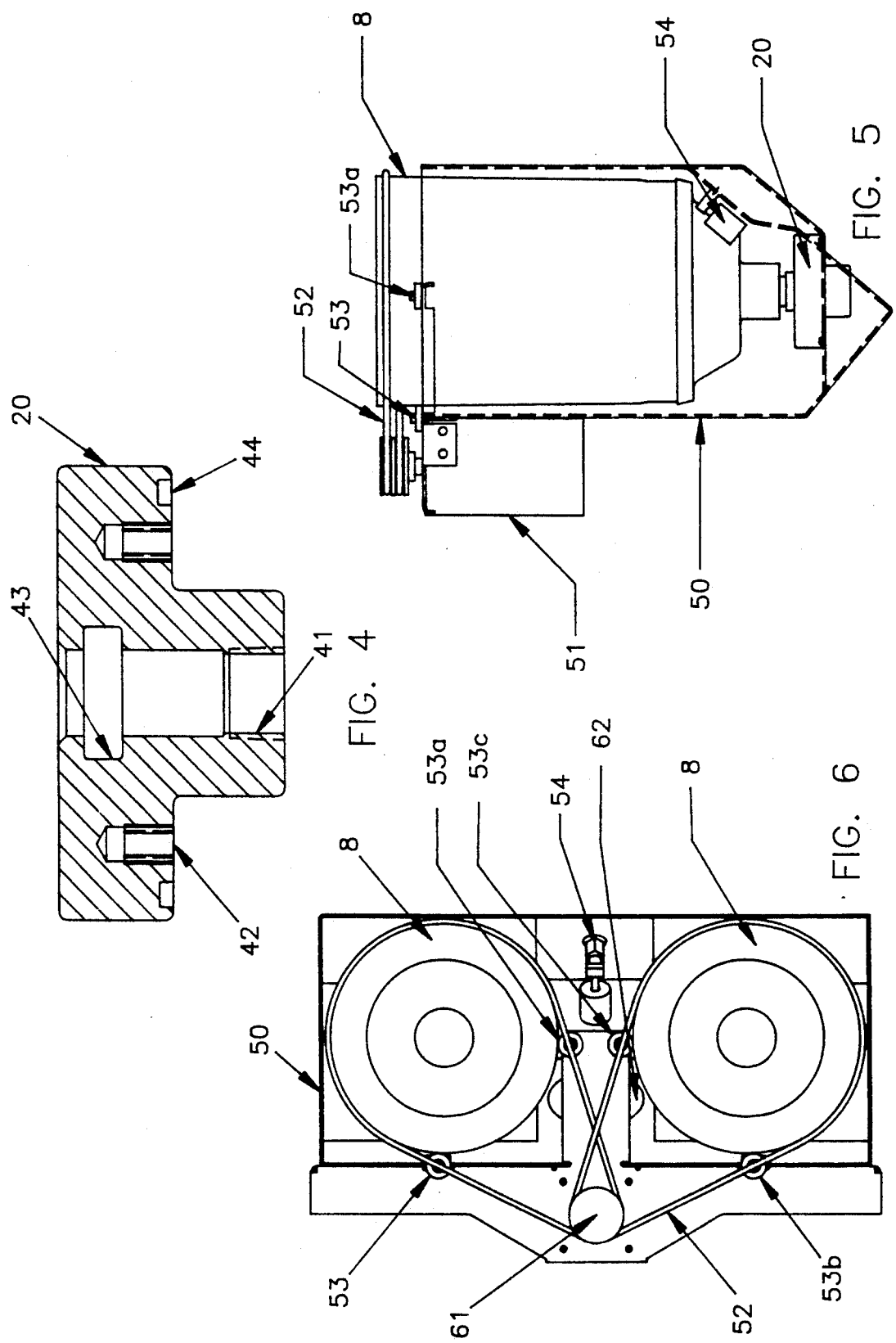

PURGE

| ROCKER # | 1 | 2 | PHASE-TIME (SEC) |
|---|---|---|---|
| | OPEN | OPEN | 0.50 |
| | OPEN | CLOSED | 0.75 |
| | CLOSED | OPEN | 1.00 |
| | CLOSED | CLOSED | 1.25 |

MIX

| ROCKER # | 3 | 4 | |
|---|---|---|---|
| | OPEN | OPEN | 2.50 |
| | OPEN | CLOSED | 3.50 |
| | CLOSED | OPEN | 4.75 |
| | CLOSED | CLOSED | 6.00 |

DWELL

| ROCKER # | 5 | 6 | |
|---|---|---|---|
| | OPEN | OPEN | 0.25 |
| | OPEN | CLOSED | 2.00 |
| | CLOSED | OPEN | 4.00 |
| | CLOSED | CLOSED | 6.00 |

RINSE

| ROCKER # | 7 | 8 | |
|---|---|---|---|
| | OPEN | OPEN | 3.00 |
| | OPEN | CLOSED | 4.50 |
| | CLOSED | OPEN | 6.25 |
| | CLOSED | CLOSED | 8.00 |

SELF-CLEAN SETTINGS

| ROCKER # | 1 | 2 | CYCLE TIMING |
|---|---|---|---|
| | NOT USED | OPEN | EVERY 24 HOURS |
| | | CLOSED | EVERY 8 HOURS |

| ROCKER # | 3 | 4 | |
|---|---|---|---|
| | OPEN | OPEN | EVERY 256 CYCLES |
| | OPEN | CLOSED | EVERY 128 CYCLES |
| | CLOSED | OPEN | EVERY 64 CYCLES |
| | CLOSED | CLOSED | DEFAULTS TO TIME CYCLE SETTING ON ROCKER #2 |

AUTOMATED CLEANSING CHAMBER

CROSS REFERENCES

The present invention incorporates by reference U.S. Pat. No. 4,817,651 (1989) to Crisp et al. and U.S. Pat. No. 4,925,495 (1990) to Crisp et al.

FIELD OF THE INVENTION

The present invention relates to revolving cylindrical cleansing chambers especially well suited to washing hands.

BACKGROUND OF THE INVENTION

Touchless automated handwashing devices are designed to provide the proper amount of antimicrobial solution in a set time. The present art uses recommended handwashing methodology. Additionally these systems diminish the deterrent effects of friction and irritation associated with frequent manual handwashing.

Medical experts have concluded that automated handwashing increases handwashing compliance and reduces the risk of infection. Other industries including food service, food processing and clean room manufacturing use automated handwashers to help eliminate the spread of infection.

U.S. Pat. No. 4,925,495 (1990) to Crisp et al. teaches a method and apparatus to periodically circulate a cleaning liquid through the cleansing chamber of a hand washing system. A timer, counter and valve assembly injects the cleaning liquid into the cleansing chamber after a preset number of washing cycles.

U.S. Pat. No. 4,817,651 (1989) to Crisp et al. teaches a touchless handwashing system having a pair of rotating cylinders. These cylinders contain slits which function as rotating nozzles. The rotating cylinder is housed in a basin for the wash, rinse and cleaning liquids. The rotating nozzles provide a helical array of spray to the hands starting at the forearm and finishing at the finer tips. A control center allows the user to select and program the desired cleansing cycle. A soap, disinfectant and rinse cycle is shown. The invention pioneers the use of rotating nozzles to simulate pulsating or varying pressure cleansing fluid jets which produce a trampoline effect to remove dirt. Considerably less effort and energy is required to rotate cylinders than to vary pressure.

Various fixed nozzle handwashing systems are known in the art including automatic sensing devices, wash, rinse, dry cycles and controllers to count wash cycles.

The present invention improves upon all the known art by integrating on a rotating nozzle system automatic sensing means, multi function control means, programmable purge, wash, dwell, rinse and clean cycles, a ten second complete wash and rinse cycle with precise chemical formula and precise volumetric control of wash and rinse water to eliminate residue on the hands. Thus, a single commercially viable invention is disclosed having application in various industries including medical, school, food service and food processing.

SUMMARY OF THE INVENTION

The primary object of the present invention is to provide a highly efficient low-water and energy consumption rotating nozzle cleaning system.

Another object of the present invention is to provide a programmable state of the art controller on a rotating nozzle cleaning system.

Another object of the present invention is to provide no touch activation on a rotating nozzle cleaning system.

Another object of the present invention is to provide precise chemical blending for maximum cleansing without irritation on a rotating nozzle cleaning system.

Another object of the present invention is to provide precise volumetric control of a rotating nozzle cleaning system to avoid chemical residue in the rinse cycle.

Another object of this invention will appear from the following description and appended claims, referenced being had to the accompanying drawings forming a part of this specification wherein like reference characters designate corresponding parts in the several views.

BRIEF DESCRIPTION OF THE DRAWINGS

FIG. 4 is a front cross sectional view of the cylinder mount shown in FIG. 3.

FIG. 5 is a left side view of a rotating cylinder taken along line 5—5 in FIG. 1.

FIG. 6 is a top plan view of the rotating cylinders taken along line 6—6 in FIG. 1.

FIG. 7l is a front perspective view of a foot activated no touch systems.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 1:
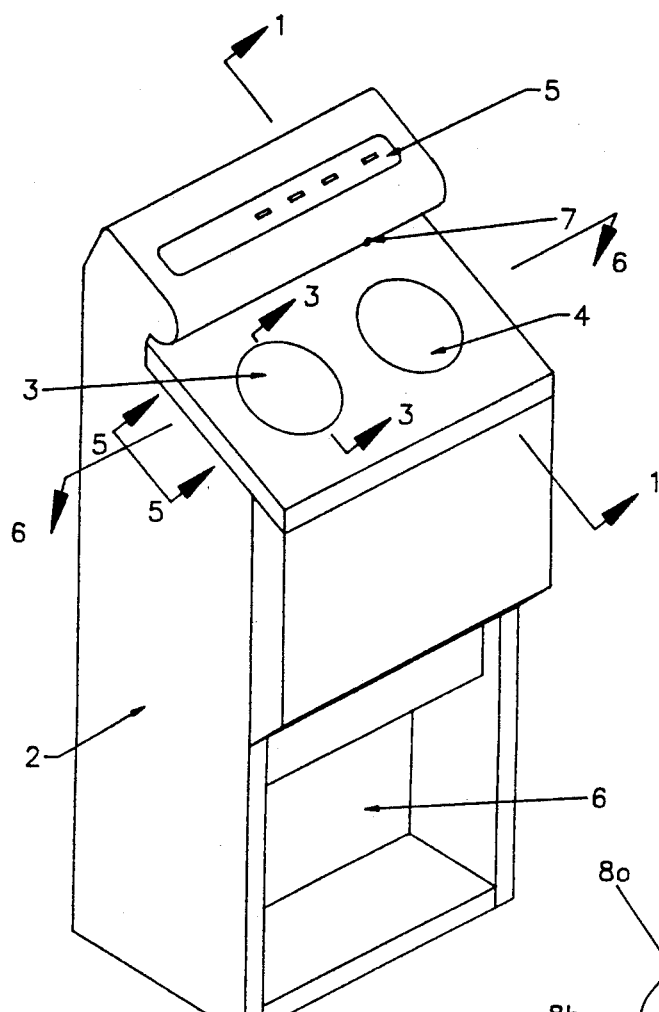
FIG. 1 is a front perspective view of a free standing cleansing unit.

Referring to FIG. 1 cleansing unit 1 is a free standing hand and forearm washing unit. Cabinet 2 includes a pair of parallel cylindrical hand openings 3,4. L.E.D. panel 5 allows the user to interface with the cleansing unit 1. An electronic controller is housed behind L.E.D. panel 5. The soap container storage area is shown at 6. A photoeye 7 senses the presence of a hand in hand opening 4 and starts the washing cycle.

Usual washing cycles range around ten seconds. The user merely inserts his hands (gloved or ungloved) into cylindrical hand opening 3,4 and receives a purge, soap, dwell and rinse cycle within around ten seconds. The purge cycle allows the water to reach the proper temperature. The soap cycle washes. The dwell cycle allows the soap and or disinfectant to kill germs, and the rinse cycle removes the soap.

Figure 2:
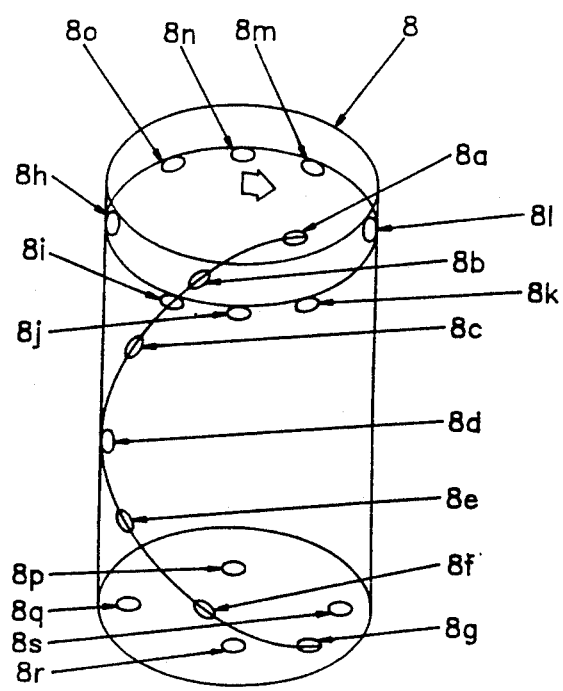
FIG. 2 is a front perspective view of a rotating nozzle cylinder.

As shown in FIG. 2 the cylindrical hand openings 3,4 each contain a rotating cylinder 8. Cylinder 8 is substantially the same as cylinder 17, FIG. 4 in U.S. Pat. No. 4,817,651 (1989) to Crisp et al., said patent being incorporated herein by reference. Rotating nozzles 8a-s are slits in the inner surface of rotating cylinder 8. Nozzles 8a-g form a helical pattern on the user's hand such that dirt is swept from the forearm to the fingertips.

Nozzles 8h-o form a water splash prevention ring around the user's forearm. Nozzles 8p-s are an improvement over U.S. Pat. No. 4,817,651. Nozzles 8p-s are fingertip cleaning nozzles.

Figure 3:
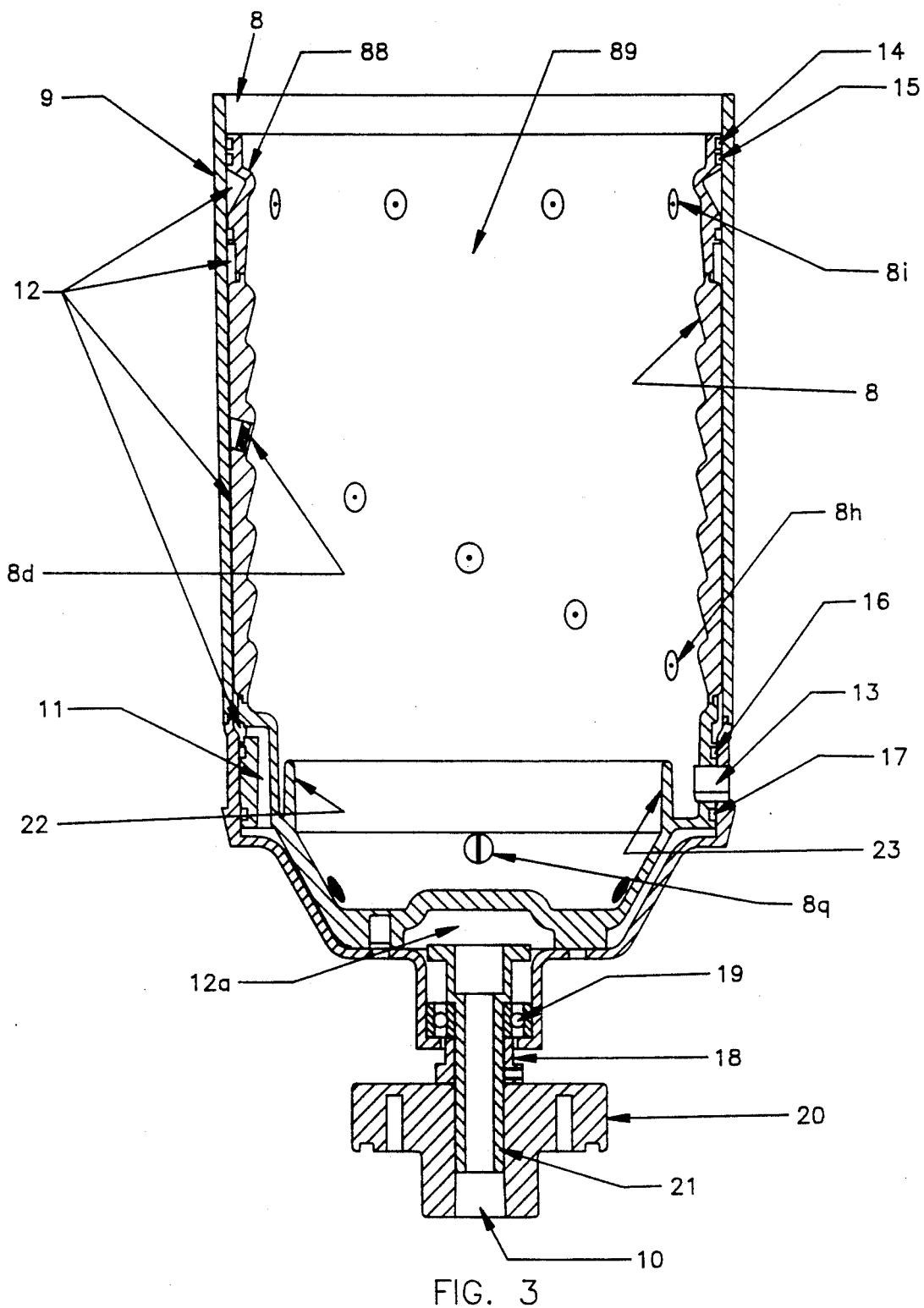
FIG. 3 is a front cross sectional view of the rotating nozzle cylinder taken along line 3—3 of FIG. 1.

Referring next to FIG. 3 rotating cylinder 8 comprises an outer cylinder 9 and an inner wall 88. Water inlet 10 feeds the washing and rinsing fluids through passage 11 into chamber 12, 12a into hand area 89 and out drain slots (s) 13. Drain protectors 22 and 23 prevent gloves or fingertips from reaching drain slot 13.

The sizing of chamber 12 is critical to proper operation. Chamber 12 holds approximately 150 milliliters of fluid. A full ten second wash and rinse cycle uses approximately 1900 milliliters of fluid. The criticality of the ratio of 150/1900 (approximately 0.08) is to minimize the presence of washing agents in the rinse cycle. If the chamber 12 is too large, then soap remains in the rinse water because the rinse cycle only lasts seven seconds or less.

Fluid is retained in chamber 12 by means of O ring grooves 14, 15, 16 and 17. Inlet water travels from inlet 10 to chamber 12a. The water is contained therein by means of cylinder lock collar 18, cylinder bearing 19, cylinder mount 20, and cylinder shaft 21. Cylinder lock collar 18, cylinder mount 20 and cylinder shaft 21 remain fixed while rotating cylinder 8 rotates.

The rotating cylinder 8 is snap mounted and easily removed for maintenance from cylinder mount 20. FIG. 4 shows O-ring grooves 43,44, mounting screw insert 42 and threaded inlet 41 of cylinder mount 20.

FIG. 5 shows how rotating cylinder 8 and cylinder mount 20 are housed in a drain basin 50. If the water level in the basin 50 reaches the float switch 54, then shut off occurs to prevent backwash into rotating cylinder 8. Drainage from basin 50 is simply a gravity drain (not shown). Motor 51 rotates rotating cylinder 8 by means of drive belt 52 and idler bearings 53, 53a. Motor 51 is current limiting to prevent injury in case glove materials jam the rotating cylinders 8.

Referring next to FIG. 6 basin 50 is shown housing the two rotating cylinders 8. Motor pulley 61 drives the drive belt 52. The external idler bearings 53, 53a, 53b, 53c control the tension on the drive belt 52. The external positioning of idler bearings 53, 53a, 53b, 53c provide a smooth and safe inner surface for rotating cylinders 8 as well as ease of maintenance. Drain 62 empties all fluids from basin 50.

Figure 7A:
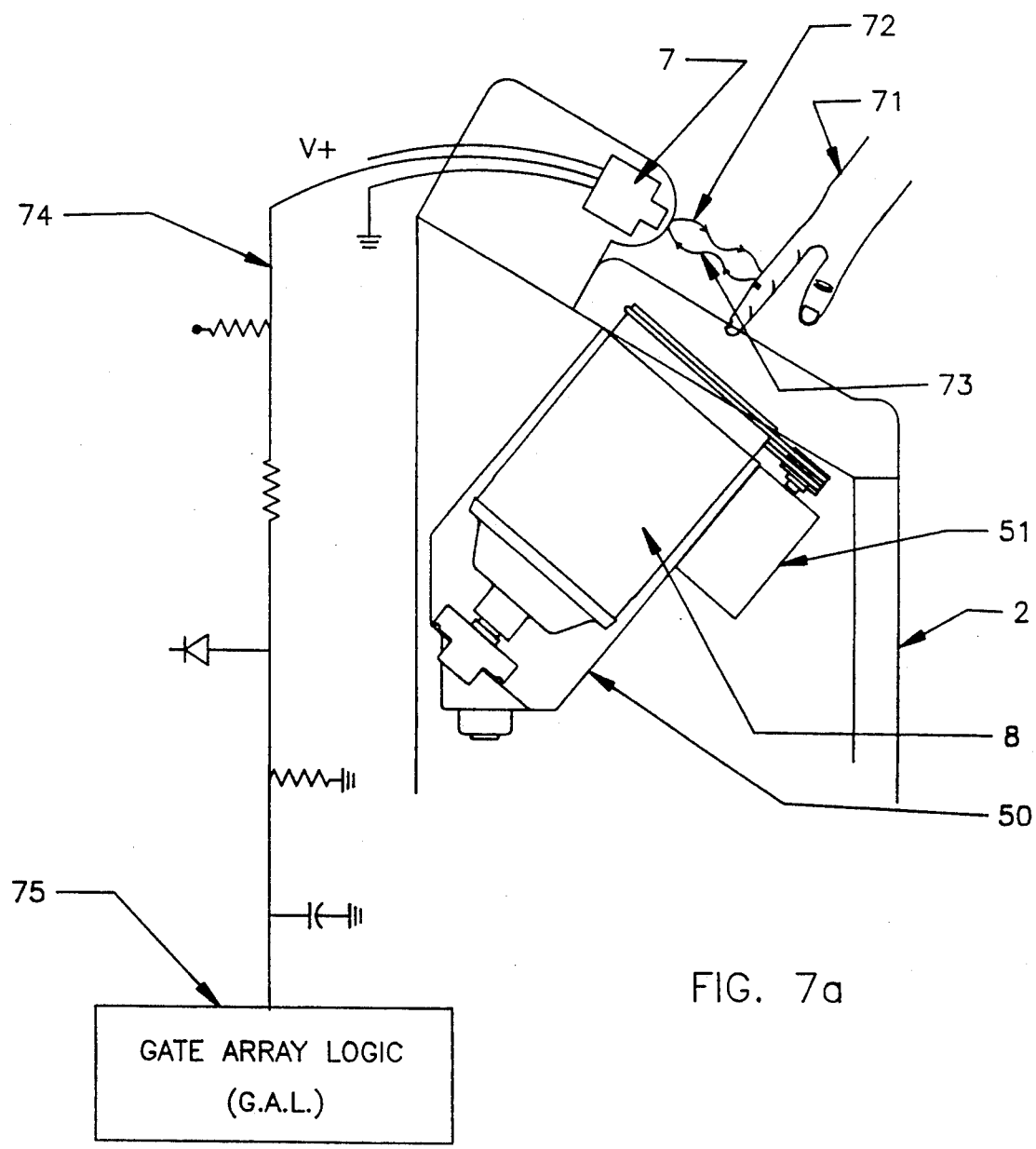
FIGS. 7a-7k are left side view of various no touch systems.

Referring next FIG. 7a cabinet 2 houses the diffuse photoeye 7. The diffuse photoeye is DC powered and sends infrared signal 72 toward the hand 71 which bounces signal 73 back to the sensing means in diffuse photoeye 7. The current sink line 74 is active when photoeye 7 senses reflected light of its own frequency 73. Upon receiving a sinking circuit from line 74 the gate array logic 75 initiates a wash cycle. The gate array logic could also be written to accept a current source from the photoeye 7 in lieu of a current sink.

Other means for no touch activation include retro-reflective photoeye sensing, convergent/divergent photoeye sensing, thru scan photoeye sensing, ultrasonic sensing, proximity sensing and foot/knee valve actuation.

Figure 7B:
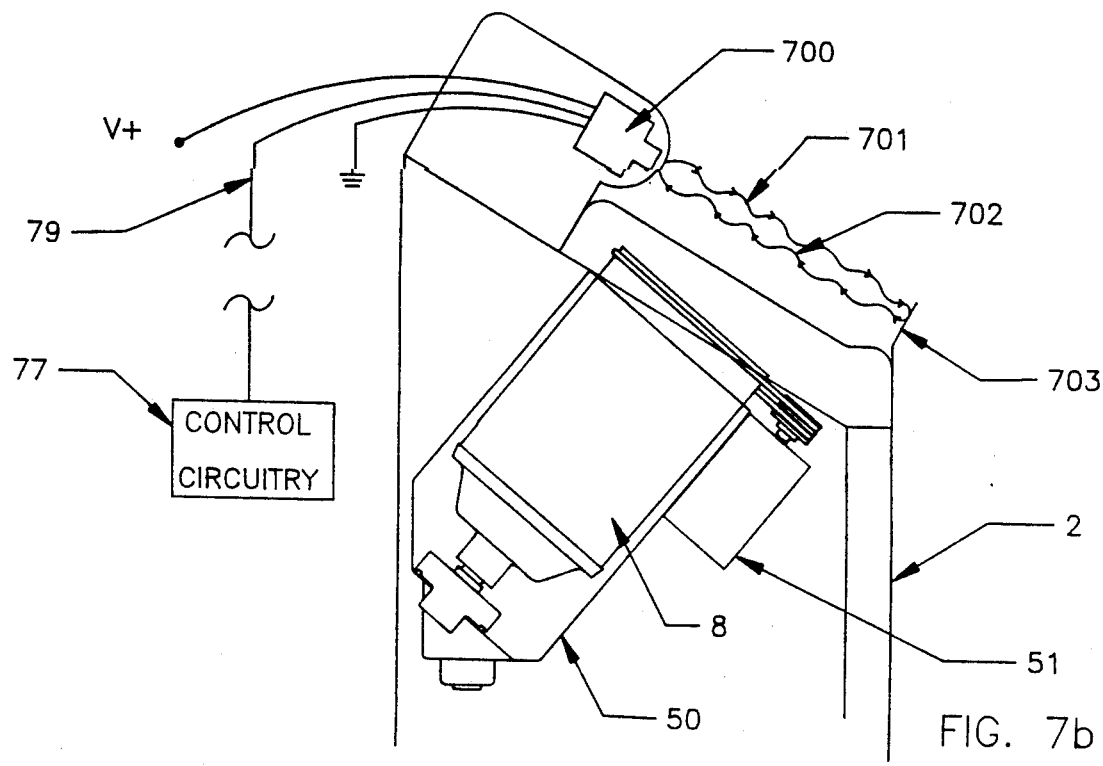
Figure 7C:
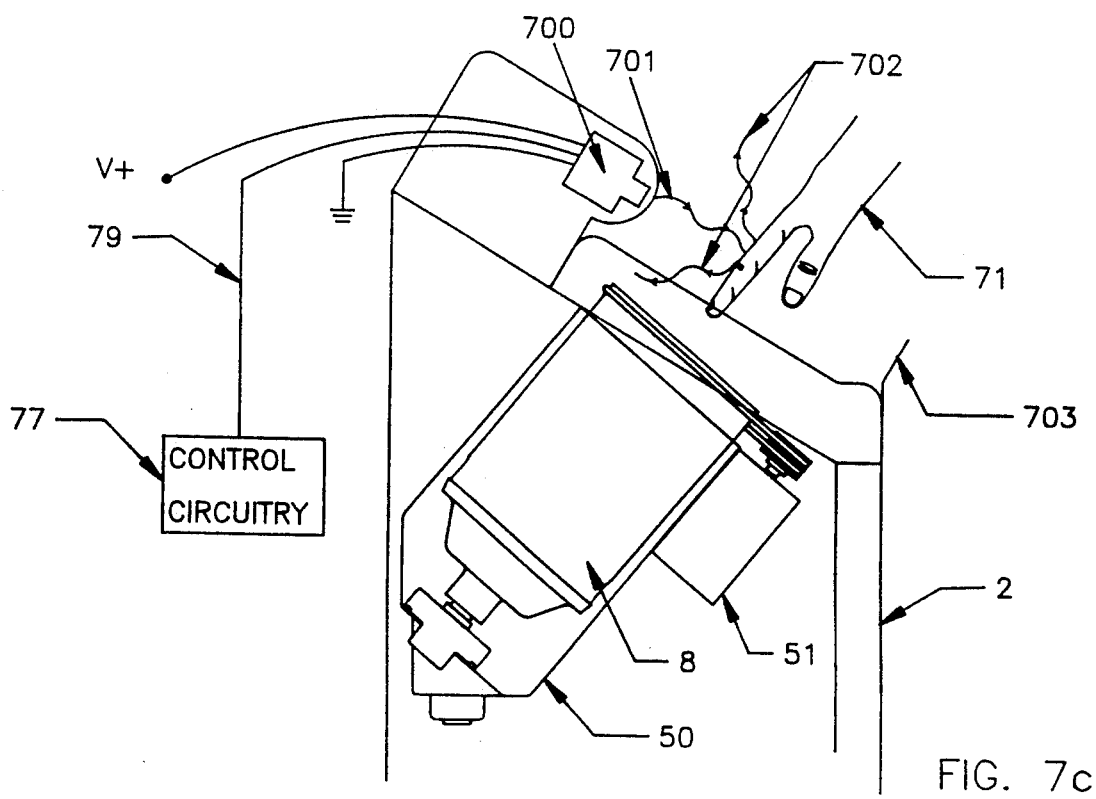

Referring to FIG. 7b a retro-reflective photoeye sensor 700 sends infra red signal 701 to reflective strip 703 and senses reflected signal 702. FIG. 7c shows hand 71 blocking signal 701 thereby preventing reflected signal 702 (representing a large amount of infra red of the frequency of signal 701) from reaching photoeye sensor 700. Current sink line 79 is sensed by control circuitry 77, and the wash cycle is activated.

Figure 7D:
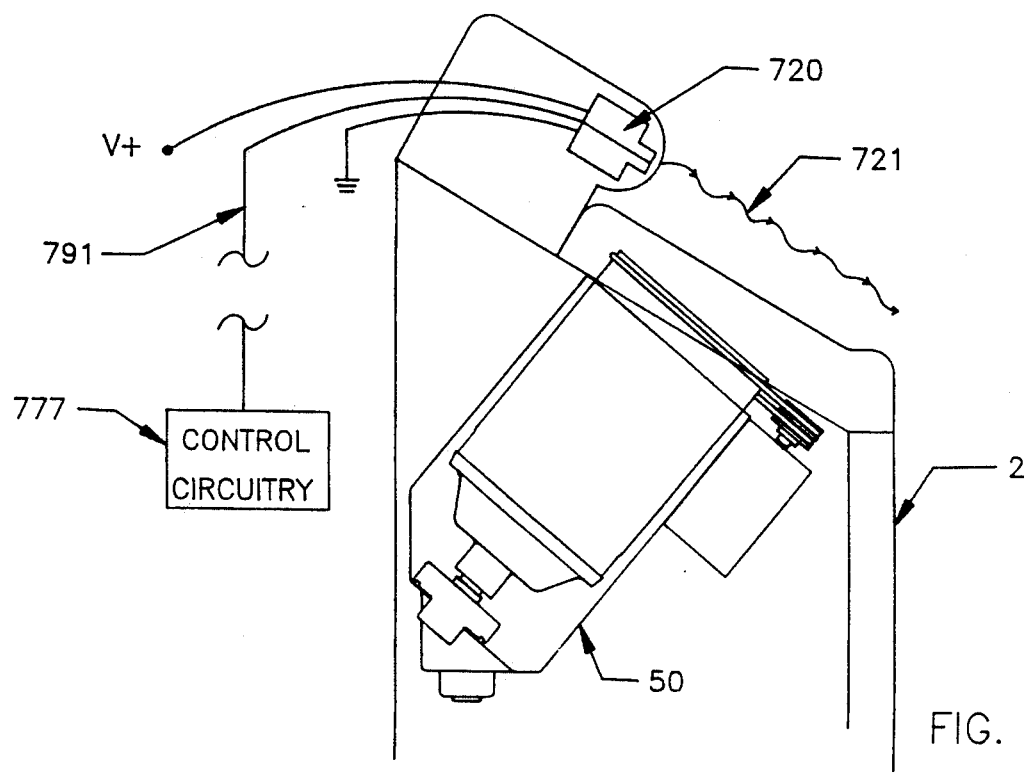
Figure 7E:
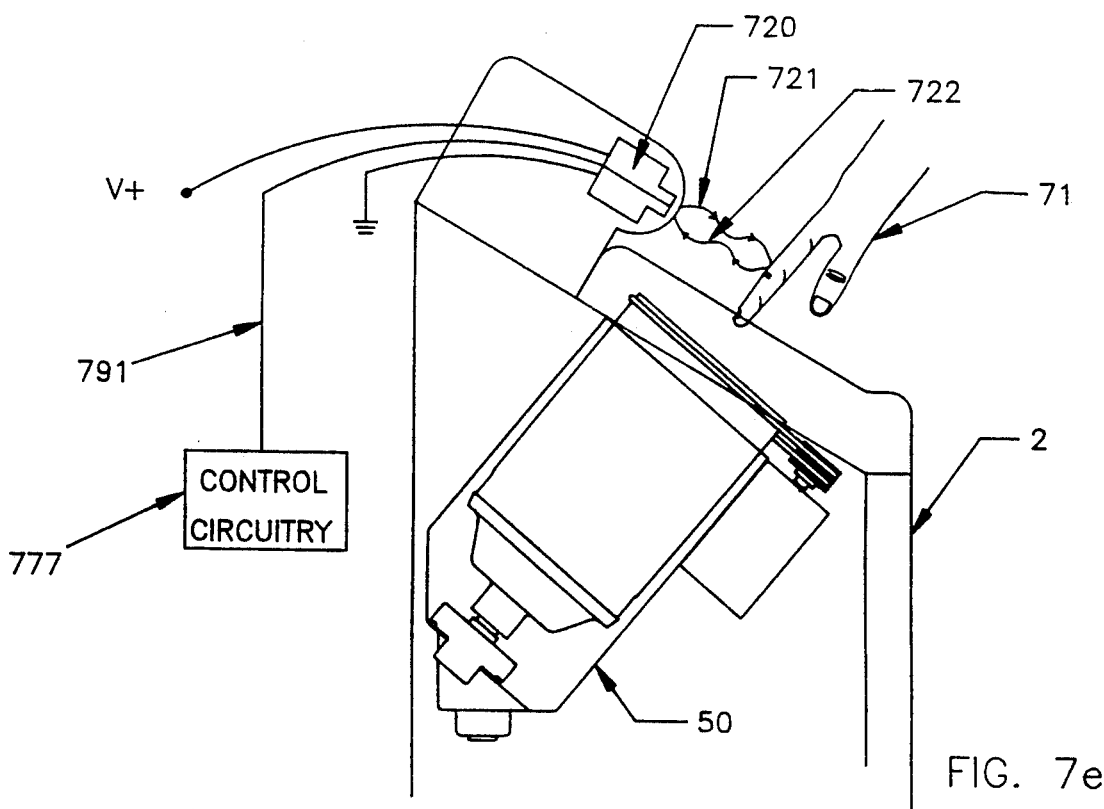

A convergent photoeye 720 as seen in FIGS. 7d, 7e operates identically as a diffuse photoeye as see in FIG. 7a except that diffuse photoeye senses reflection from large ranges such as 0 to 6 inches, whereas convergent photoeye sensor senses reflections in narrow ranges such as 5.5 to 6.0 inches. Convergent photoeye sensor 720 sends signal 721. When reflected signal 722 is sensed due to reflections from hand 71, the current sink lead 791 triggers control circuitry 777 to begin the wash cycle.

Figure 7F:
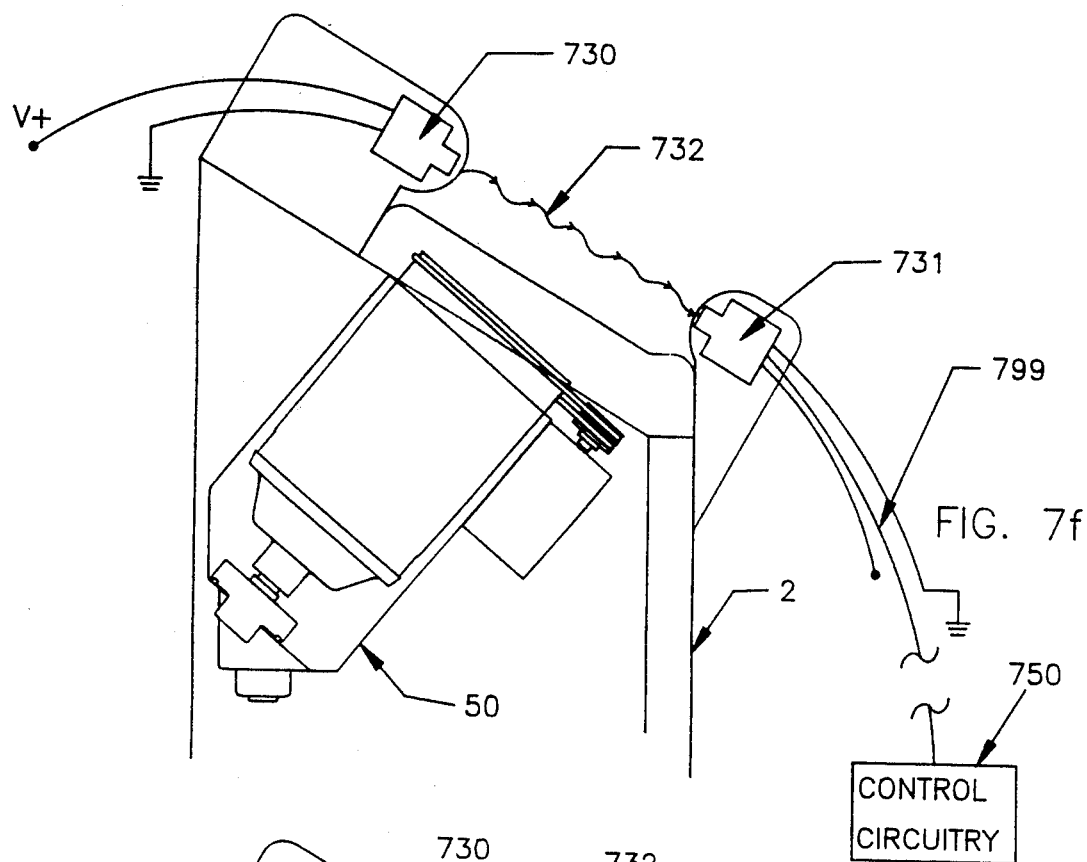
Figure 7G:
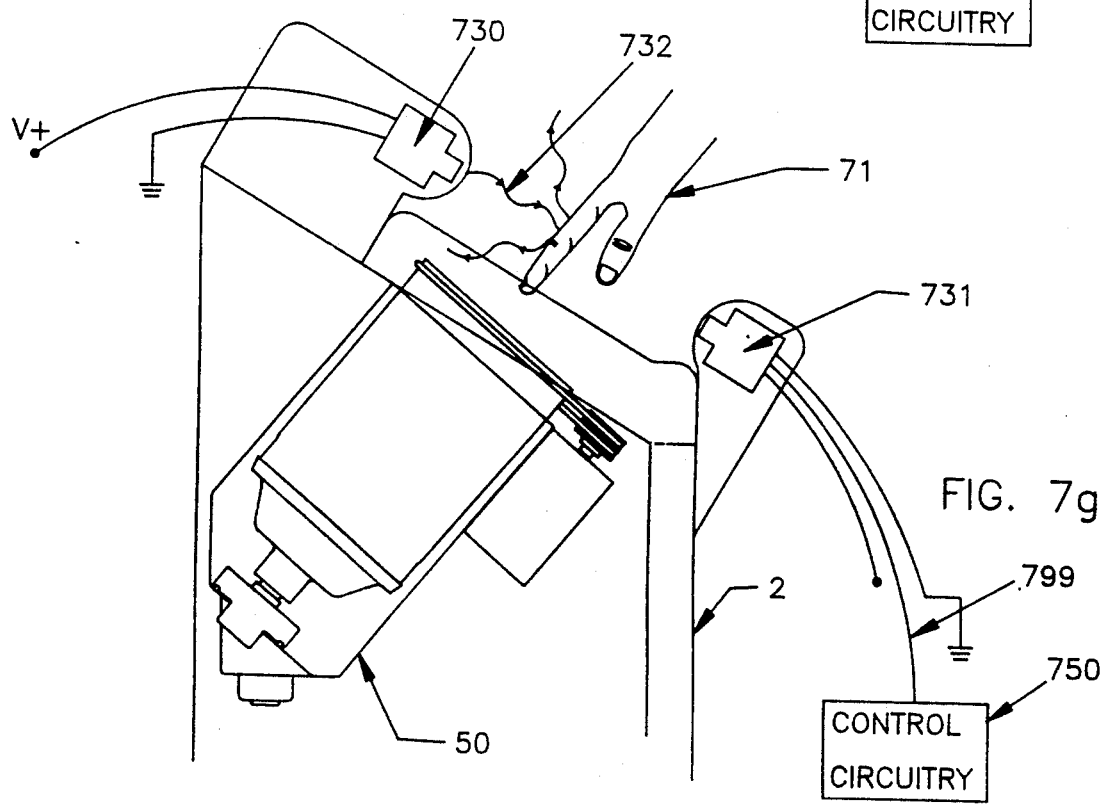

A thru scan photoeye system is seen in FIGS. 7f and 7g. Emitter 730 sends signal 732 to receiver 731. If hand 71 breaks signal 732, then receiver 731 no longer senses signal 732 and triggers current sink lead 799 to activate control circuitry 750 to start the wash cycle.

Figure 7H:
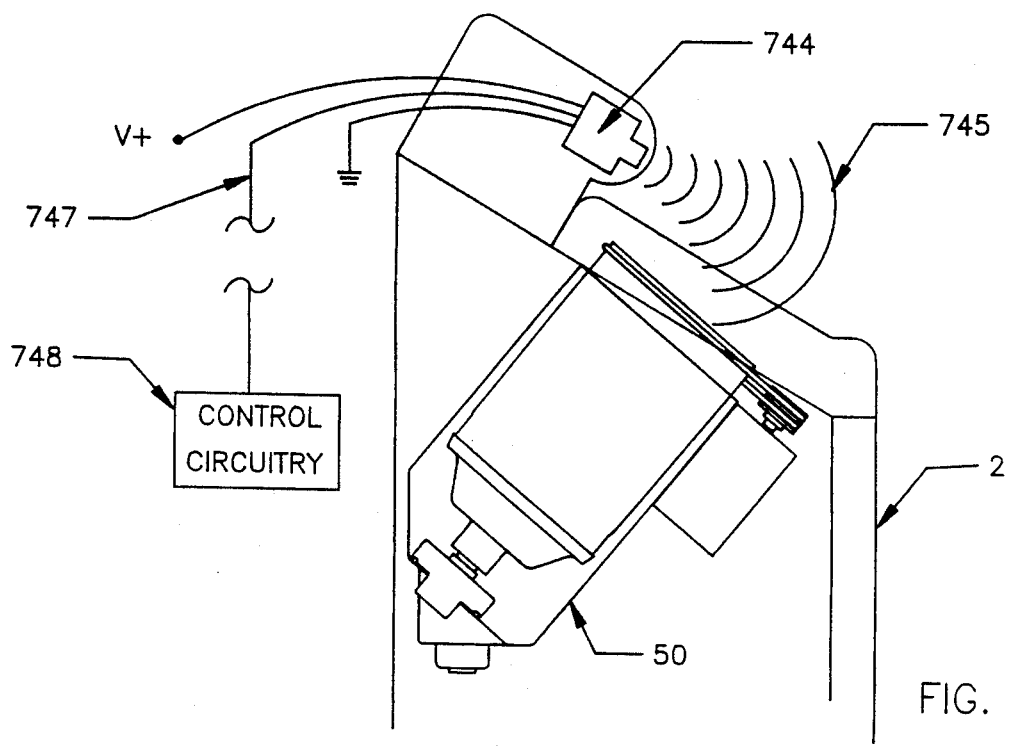
Figure 7I:
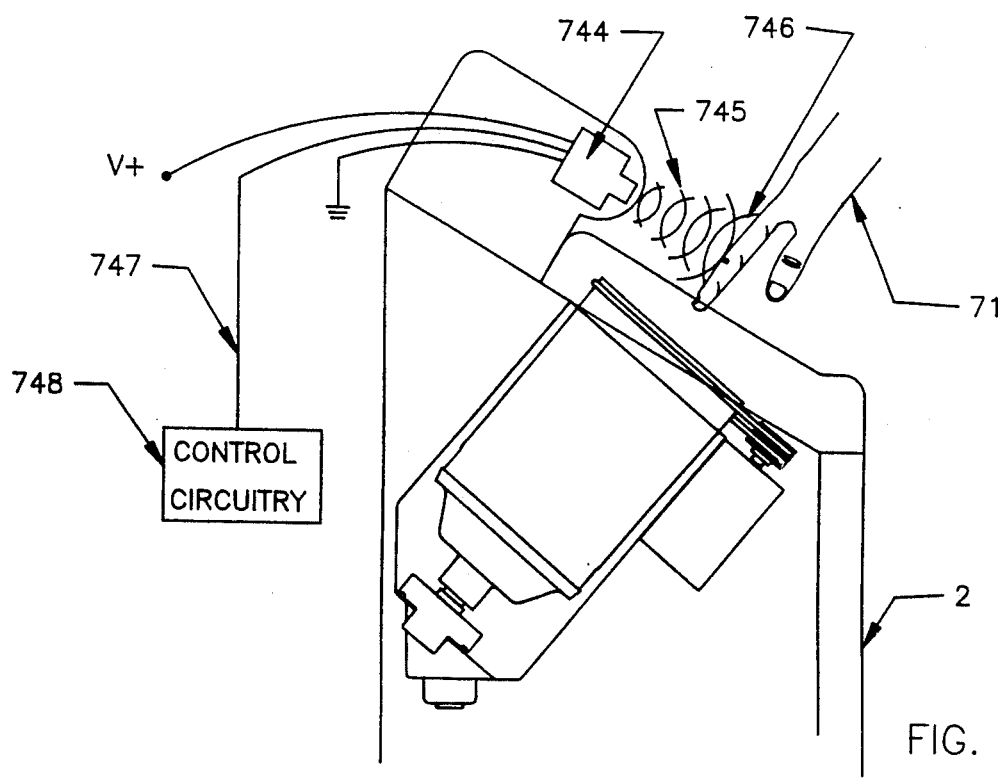

An ultrasonic system is shown in FIGS. 7h, 7i. Ultrasonic sensor 744 sends sound signals 745 at a common frequency. Hand 71 reflects sound signals 745 which become reflected signals 746 of the same frequency as signals 745. Current sink lead 747 becomes active when ultrasonic sensor 744 detects reflected signals 746. Control circuitry 748 starts the wash cycle.

Figure 7J:
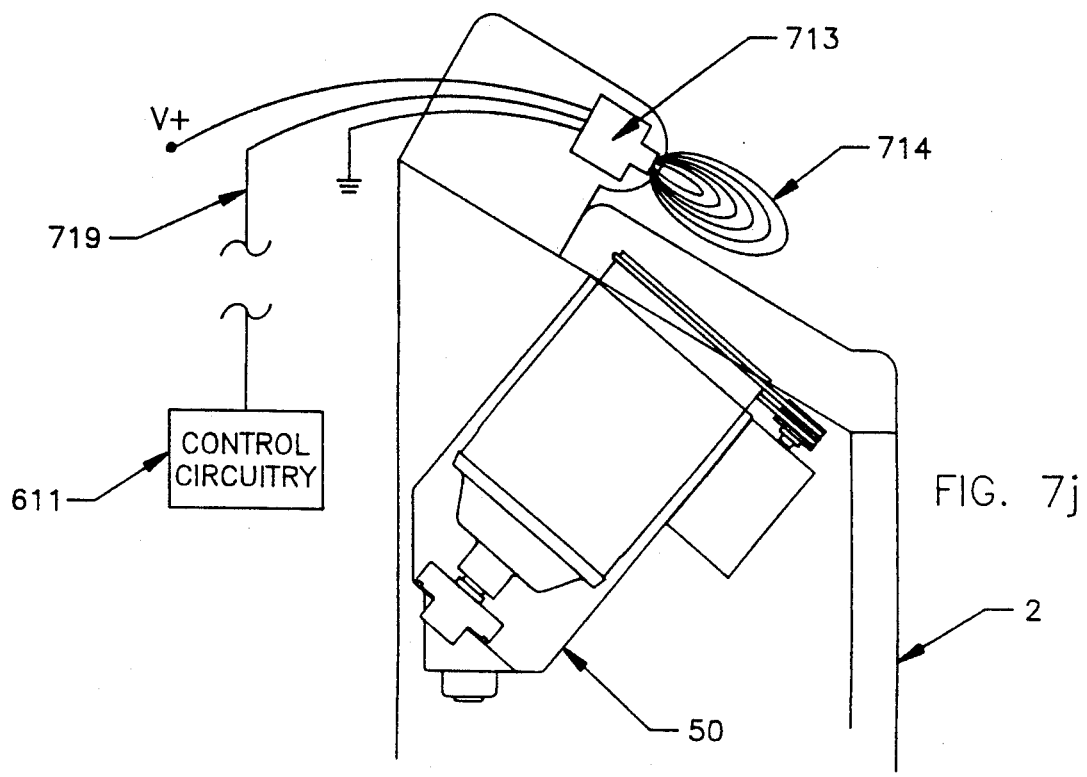
Figure 7K:
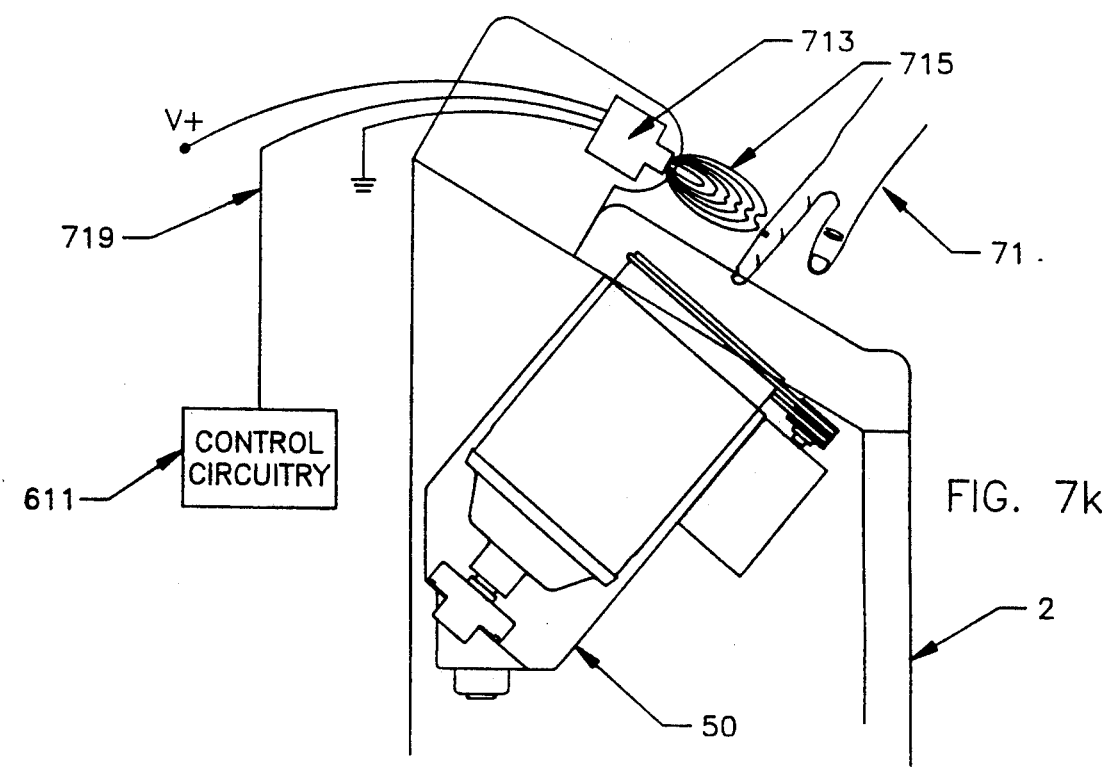
Figure 71:
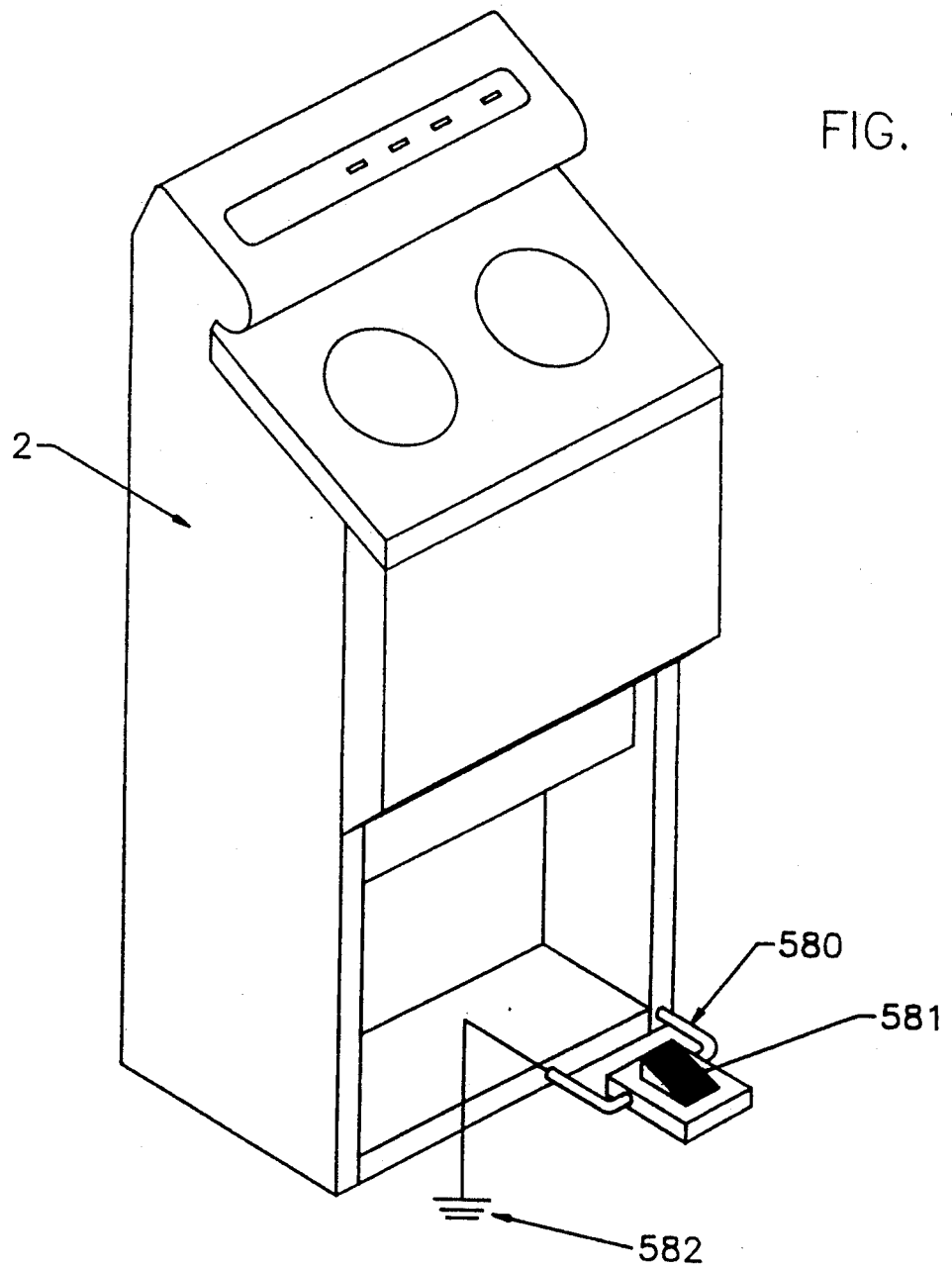

A proximity sensing system is shown in FIGS. 7j,k. Proximity sensor 713 sends out magnetic radiation waves 714. When hand 71 distorts magnetic radiation waves 714 into waves 715, proximity sensor 713 activates current sink line 719. Control circuitry 611 starts the wash cycle.

Foot activators as shown in FIG. 7l allow a no touch start of the wash cycle. The ground circuit from 580 to 582 is normally open. Current sink lead 580 goes to a gate activated controller (not shown). When switch 581 is pushed closed the current sink lead 580 is activated thereby initiating a wash cycle.

Figure 8A:
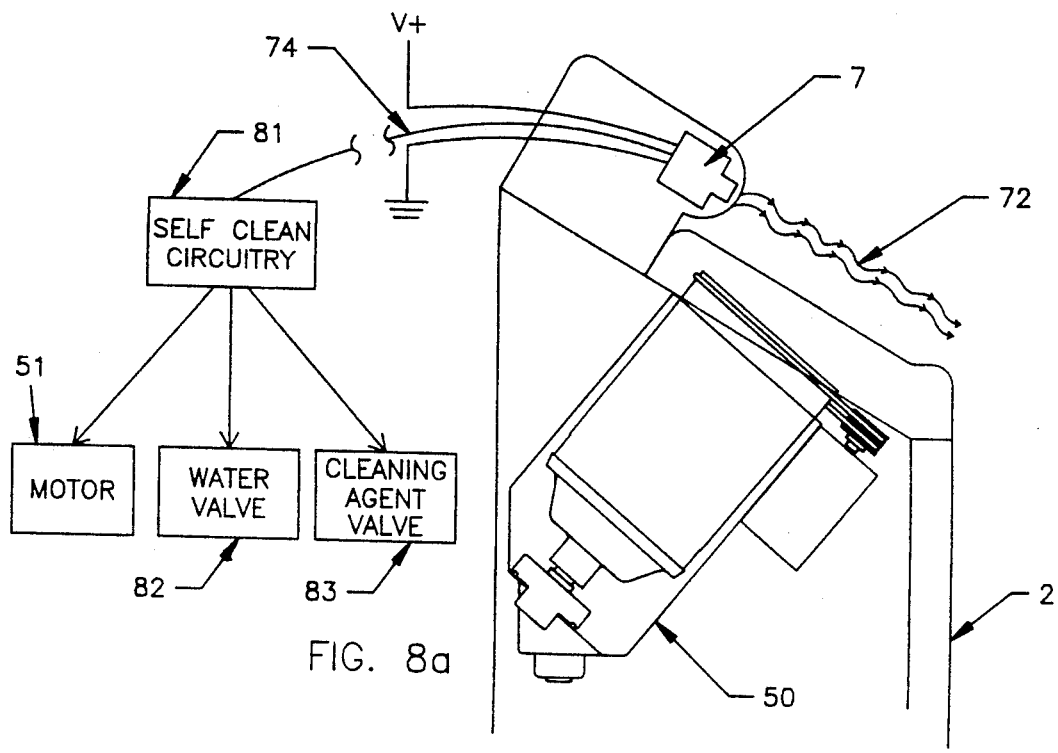
FIGS. 8a and 8b are left side view of an automatic shut down system for the self cleaning cycle.
Figure 8B:
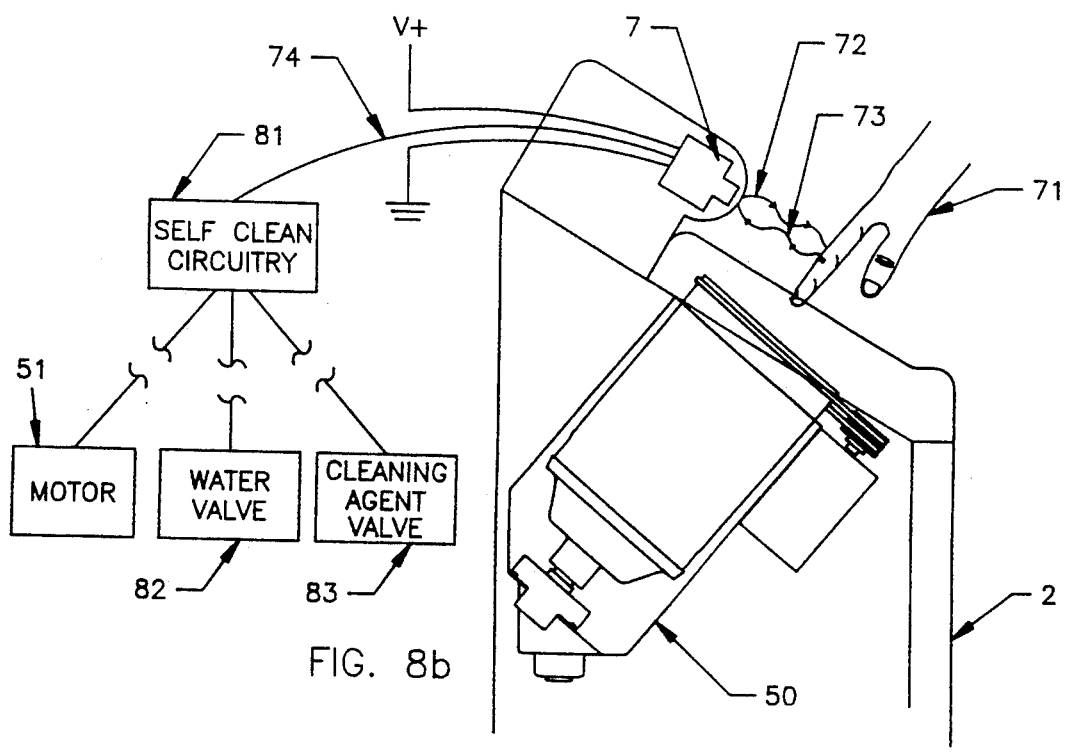

Any of the above hand sensing means can also be used to deactivate an automatic self cleaning cycle. FIGS. 8a, b show the operation of the self cleaning cycle. The self clean circuitry 81 counts the number of wash cycles before actuating the cleaning agent valve 83 to open along with the motor 51 and the water valve 82. If, however, a hand 71 is sensed by the photosensor 7 as shown in FIG. 8b., then the system shuts down and will begin the self clean cycle again only after the hand 71 has been removed.

Figure 9:
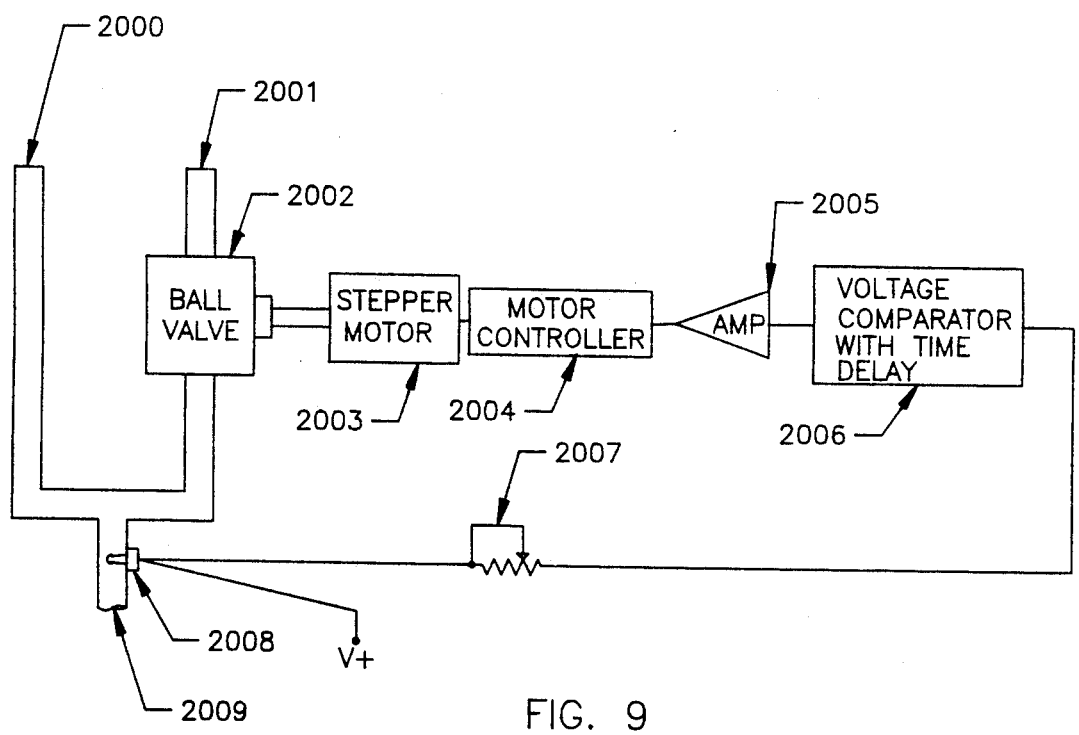
FIG. 9 is a schematic diagram of a temperature control system for the cleaning system.

Referring next to FIG. 9 a wash water temperature control system is shown. Hot water inlet 2000 is mixed with cold water inlet 2001 to produce mixed water outlet 2009. Thermistor 2008 senses outlet water temperature and changes resistance with temperature. The variable potentiometer 2007 is used to set temperature limits. The resistance of variable potentiometer 2007 and thermistor 2008 is sensed by voltage comparator 2006. A time delay in 2006 is used to allow stabilization of the outlet water 2009 with thermistor 2008. When the temperature of the outlet water 2009 is beyond preset limits, the voltage comparator sends a signal amplified by amplifier 2005 to the motor controller 2004 which causes the stepper motor 2003 to open or close the ball valve 2002.

The preferred wash chemical used for hand washing is chlorhexidine gluconate (CHG). The system goal is to effectively reduce microbial populations on the hands in one ten second wash cycle without causing skin irritation. The most effective concentration of CHG by volume mixed with water is 0.001%–0.0052%. The 0.0052% concentration is 10 milliliters per one cycle where one cycle uses one half gallon or 1892 milliliters of water. Microbial populations tested 96.37 to 99.98% reduction with the 0.001% to 0.0052% concentration with variances for water pressure and cycle time.

Figure 10A:
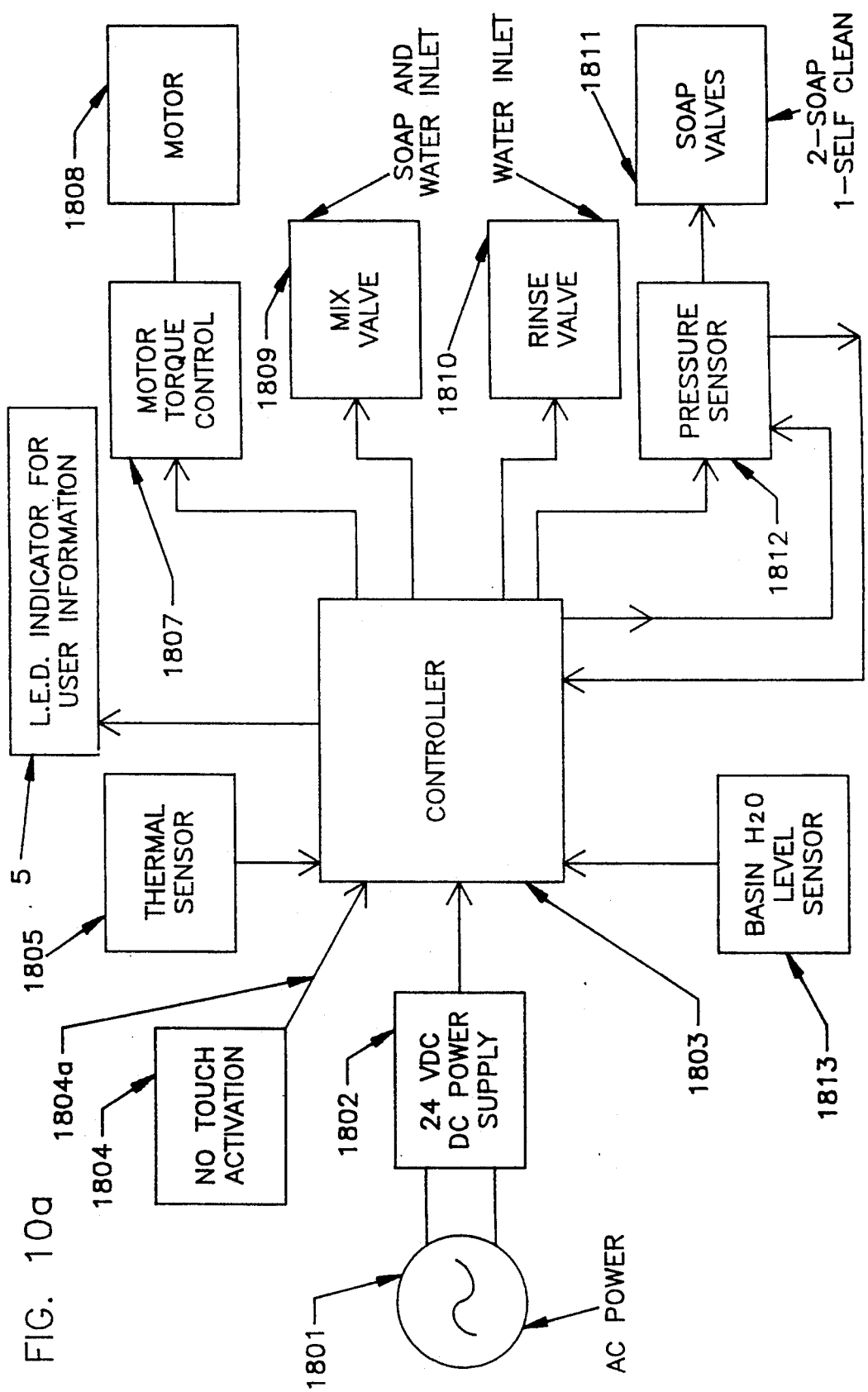
FIG. 10a is a block diagram of the controller and sensors.

Referring to FIG. 10a the flow chart illustrates the electronic module 1803 as powered by converted AC power 1801 to 24 V/DC power 1802. Once on, the no touch activation 1804 gives a continuous signal thru the current sink line 1804a to the electronic module 1803. As the thermal sensor 1805 sends a signal to the electronic module 1803, anti-scalding is in effect. Thus shut down occurs for too high a temperature.

If the no touch activator 1804 is triggered, the electric module 1803 will communicate with different components of the invention. The L.E.D. indicator for user information on panel 5 is to warn or inform the user during operation. The motor 1808 which powers the cylinders 8 (FIG. 5) has a motor torque control 1807 with a current limit chip to prevent finger injury. The mix valve 1809 for soap and water, the rinse valve 1810 for water only, or the soap valves 1811 for soap or self clean in accordance with the pressure sensor 1812 can be operated by the electronic module 1803. The pressure sensor 1812 is a transducer which senses from 0 psia to 14.7 psia. It can communicate to the electronic module 1803 if a problem occurs in the pressure. A basin water level sensor 1813 has a float switch that will send a signal to the electronic module 1803.

Figure 10B:
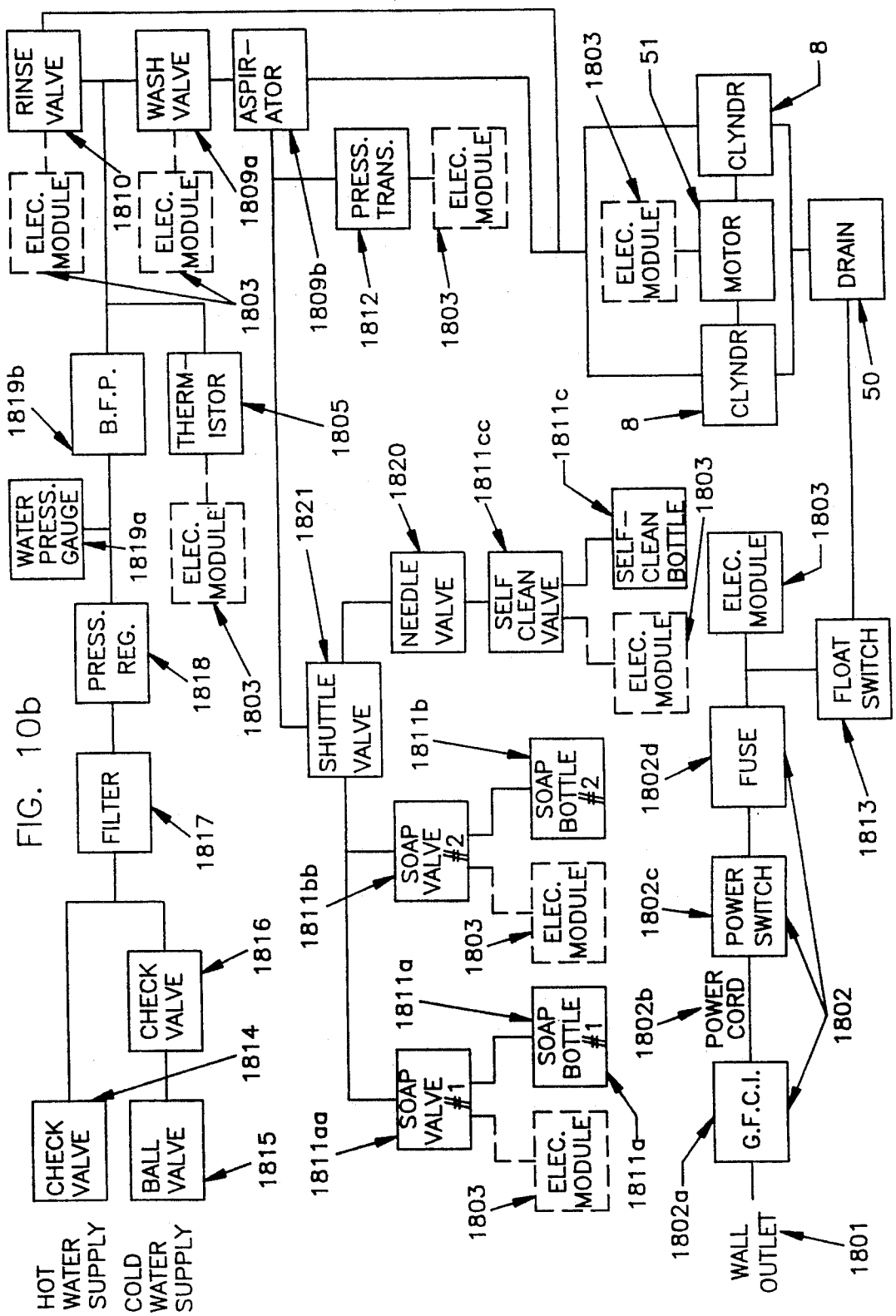
FIG. 10b is a block diagram of the controller logic.

FIG. 10b will allow us to move thru a cycle of the invention at any state. The hot water supply enters the machine through a one-way check value 1814. Cold water enters the machine first through a ball valve 1815 and then through a one-way check valve 1816. The two check valves 1814 and 1816 prevent the hot and cold water from mixing outside of the hand washing device. The hot and cold water then join together and enter a filter 1817 which removes particulates. (Note: the temperature of the water is controlled by the position of the cold water ball valve 1815 which can range from fully open (low temp) to fully closed (high temp)).

Water exiting the filter 1817 enters a pressure regulator 1818 and water pressure gauge 1819a by which the operating pressure of the machine is set. Water then enters and flows through a backflow preventer 1819b which protects the potable water supply from contamination with cleaning chemicals. After the backflow preventer 1819b, the water flows around a thermistor probe 1805 which is mounted in the flow stream. The thermistor 1805 works in conjunction with the electronic module 1803 to allow the machine to operate only when the water temperature at the thermistor 1805 probe is at or below a preset limit—usually 120 F. If the water temperature exceeds this limit the water valves 1810 and 1809a are closed by the electronics module 1803 to prevent scalding the user.

Non-scalding water will pass the thermistor 1805 and enter a tee. The rinse circuit of the tee passes through the rinse solenoid valve 1810, to prevent soap from being mixed. The rinse cycle is controlled by the electronic module 1803. The soap mixing leg of the plumbing circuit (FIG. 10b) allows the water to pass through a wash solenoid valve 1809a which is controlled by the electronic module 1803 before it gets to the aspirator 1809b. The aspirator 1809b is a device which creates a suction at the expense of the water pressure.

The vacuum signal is used to draw soap from their containers and mix it with the water stream. Soap is drawn from either solution container 1811a or solution container 1811b by solenoid 1811aa or 1811bb respectively. The electronic module 1803 chooses either solution container if the other is empty. When either solutions solenoid valve 1811aa or 1811bb is open it will remain open for a preprogrammed amount of time (nominal=2.5 sec) at the beginning of the wash cycle. Soap is allowed to enter the water stream as long as either solution solenoid valve 1811aa or 1811bb stays open. To prevent soap from mixing with the self clean mixtures a shuttle valve 1821 is used after solution solenoid 1811aa and solution solenoid 1811bb. On a preprogrammed basis, the electronic module 1803 will open the self-clean solenoid valve 1811cc and allow self-cleaning fluid (preferably ammonium chloride) to flow from its solution container 1811c through the self-clean solenoid valve 1811cc and the shuttle valve 1821 into the aspirator 1809b. Soap will join the water stream into the rotating cylinder 8 and then to the system drain 50 (see U.S. Pat. No. 4,925,495).

The shuttle valve 1821 allows the use of three different fluids 1811a or 1811b and 1811c with only a single aspirator 1809b. Soap or self-cleaner in the plumbing between the shuttle valve 1821 and the aspirator is pressure monitored by a pressure transducer 1812 installed in the line. This pressure transducer 1812 creates a variable voltage signal inversely proportional to the absolute pressure of the fluid. The electronic module 1803 will sense this voltage signal and thereby determine the amount of soap flowing. It will alert the user at panel 5 if any anomalies are found (e.g. empty soap bottle) (see FIG. 11). All water mixture exiting the aspirator 1809b and all water flowing through the rinse circuit of the plumbing flows directly to the rotating cylinders 8 and out the series of nozzles 8a–8 s located on the inner surface of the cylinders 8. At this point the gauge pressure of the water stream drops to zero. Drain water exists the cylinder through the drain slot(s) 13 and is collected in the drain basin 50 and allowed to drain to the facility sewer. The water level in the drain basin 50 is monitored from the basin water level sender 1813 by a float switch which signals the electronic module 1803 of a high water level. The electronic module 1803 will then stop the flow of pressurized water in the plumbing circuit FIG. 10b to prevent a drain basin 50 overflow. Power is obtained to a handwashing device when connected to AC power at the wall outlet 1801. Its 24 v DC power supply 1802 is present after moving through a ground fault interrupt 1802a, power cord 1802b, power switch 1802c and a fuse 1802d before reaching the electronic module 1803.

Figure 11:
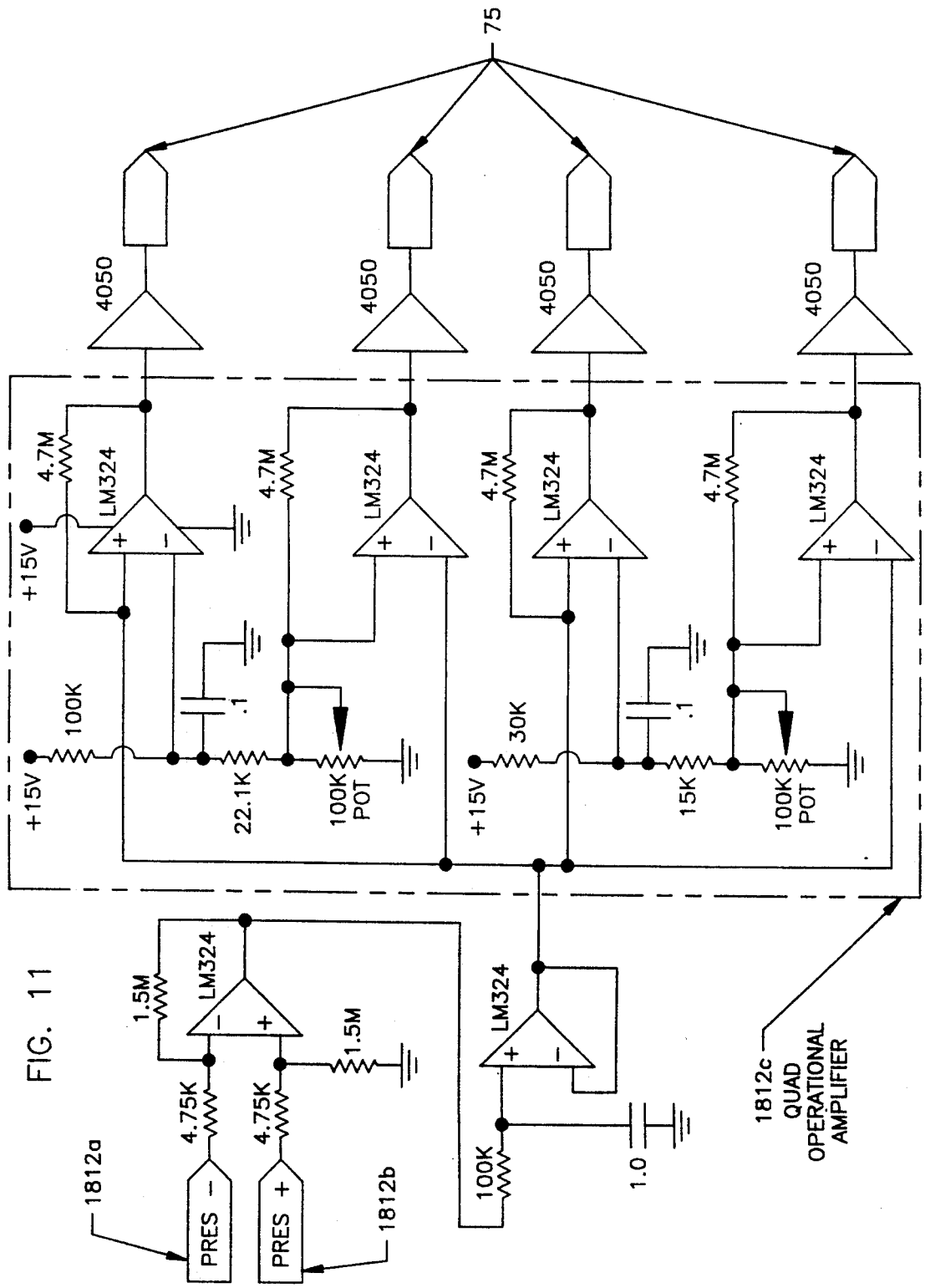
FIG. 11 is an electronic schematic of the pressure sensing system.

Viewing FIG. 11 illustrates the incorporation of a pressure sensor circuit to monitor soap flow. The pressure sensor 1812 is a transducer which converts the pressure in the soap line into a voltage 1812a and 1812b. The voltages Pres− and Pres+ respectively, are fed to a low power quad operational amplifier 1812c whose output is fed to the state array logic 75 of the electronic module 1803 (FIG. 10b). The circuit of FIG. 11 will detect an empty soap bottle, or a malfunctioning solenoid valve (1811aa, 1811bb, 1811cc of FIG. 10b) or a moderate deviation in soap flow from the factory setting.

Figure 12:
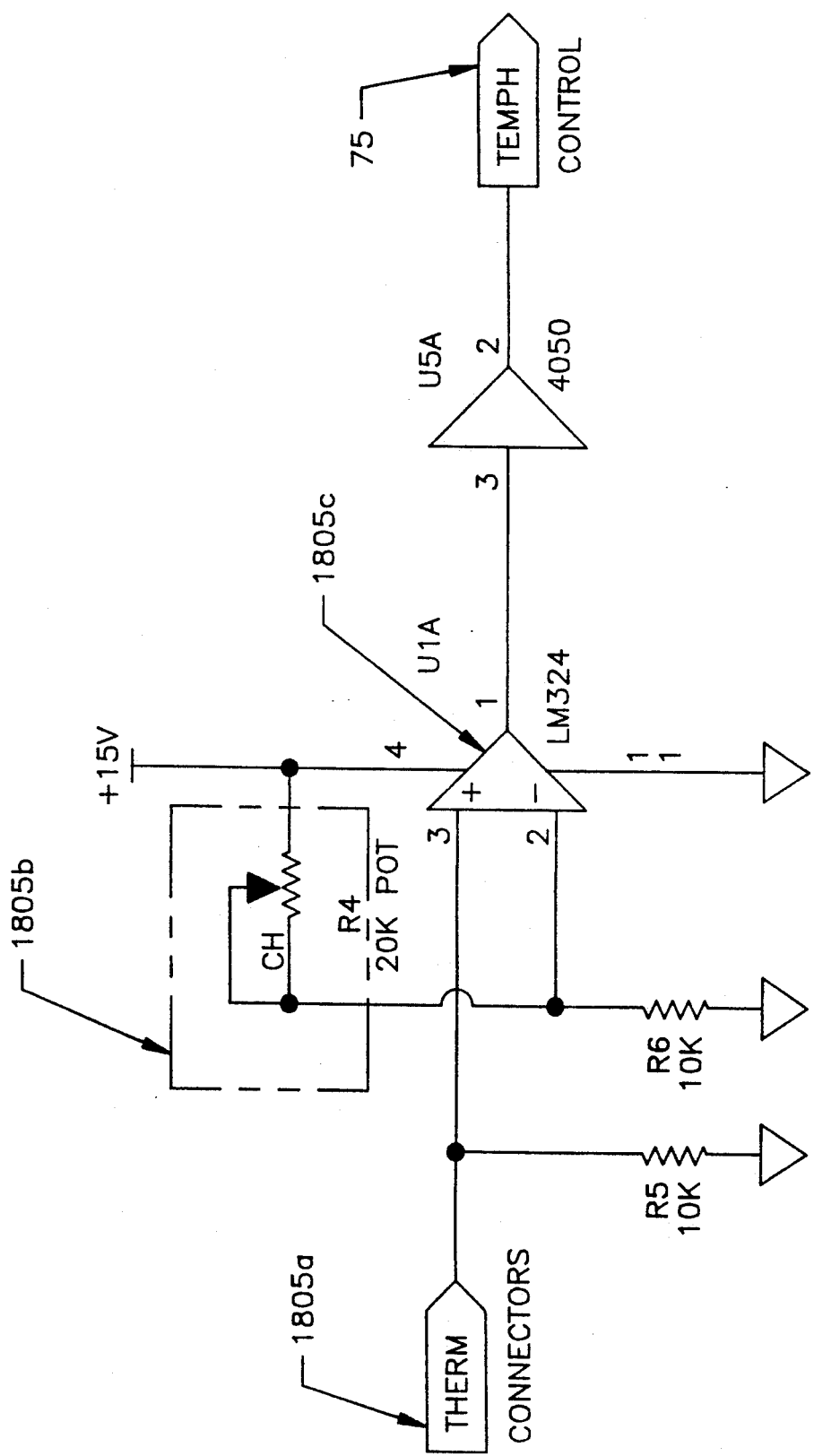
FIG. 12 is an electronic schematic of the thermistor sensing system.

FIG. 12 shows a circuit diagram that gives the cleansing unit the capabilities of sensing an over temperature condition in the incoming water. If the thermal sensor 1805 (FIG. 10b) detects incoming water over the set conditions, then the system will shut down to prevent scalding the user. The thermistor in the water stream varies resistance with temperature. This changing resistance will cause the input 1805a to the low power quad operational amplifier 1805c to become unbalanced when the water temperature exceeds a set limit (the limit is set by a variable potentiometer 1805b). When the input to the op-amp 1805c is unbalanced, the output becomes positive and is fed to the gate array logic 75 which shuts the water valves 1809, 1810 (FIG. 10b) and turns the motor 51 (FIG. 10b) off and alerts the user at the panel 5 (FIG. 1) to the over-temperature condition via a flashing L.E.D. on the panel 5 (FIG. 1).

Figure 13:
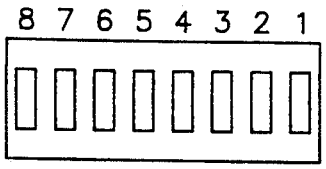
FIGS. 13 and 14 are charts of the D.I.P. switch settings on the controller.

Looking at FIG. 13 reviews four possible phases to a handwash cycle. These are purge, wash, dwell and rinse.

Time durations of each of these phases are adjustable with a (Dual Incline Project) DIP switch located on the printed circuit board S2 (FIG. 13).

Figure 14:
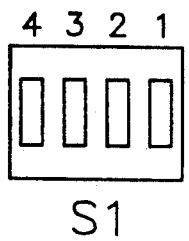

S1 (FIG. 14) of the self-clean cycle for the hand-cleaning device has adjustable DIP switches. These DIP switches are programmed to activate based on a cumulative count of hand wash cycles (for high usage application) or on a temporal basis (for low usage application) of either every 8 or 24 hours.

We claim:

1. In a hand and forearm cleansing apparatus, a cylinder having an inner surface forming a cleaning chamber, said cylinder being rotatable about its axis and having an open end through which the hand and forearm of the user enters the cleansing chamber, nozzle means in the wall of said cylinder, said nozzle means presenting no significant protuberances on the inner surface of the cylinder, means for conveying cleansing fluid to said nozzle means, means for rotating said cylinder, said nozzle means further comprising a series of nozzles disposed in a helical array in the cylinder wall, the disposition of the helical array of nozzles and the direction of rotation of the cylinder is such that each longitudinal strip of forearm surface is subjected to a series of sprays of cleansing fluid from said nozzle means commencing near said open end of the cylinder and progressing toward the hand, said nozzle means further comprising a plurality of nozzles to direct water inwardly of the cylinder and away from said open end of the cylinder, the axis of said cylinder is at an angle to the horizontal with the open end elevated with respect to the opposite end and means of draining fluid from the region of the opposite end of the cylinder, the cylinder further comprising an outer liner and an inner liner, said liners having a space there between to permit cleansing fluid to pass therethrough to said nozzle means, the apparatus further comprising a stationary cleansing fluid conduit communicating with the space between said liners, and said cylinder is rotatably mounted on said conduit at the end thereof opposite said open end, the improvement comprising:

said means for conveying cleansing fluid to said nozzle means further comprising a programmable controller which further comprises a programmable purge, wash, dwell, rinse and self clean cycle;

said cycles further comprising a total duration of approximately ten seconds and a total fluid consumption of approximately 2000 ml.;

said space there between further comprising a volume having a ratio of approximately 0.08 to the total fluid consumption;

said stationary cleansing fluid conduit further comprising snap mounting means for quick disconnect;

said snap mounting means further comprising a cylinder mount functioning to support said rotating cylinder;

said means for rotating said cylinder further comprising a motor and a belt disposed about said open end of the cylinder; and said means for rotating further comprising external idler bearings.

2. The cleansing apparatus of claim 1 wherein said controller further comprises a wash water temperature control means to allow a mixture of a hot water input and a cold water input to reach a preset temperature during the purge cycle and then proceed to the wash cycle.

3. The cleansing apparatus of claim 1 further comprising means to sense a user's hand in close proximity to the cleansing apparatus.

4. The cleansing apparatus of claim 3 wherein said controller further comprises self clean circuitry which counts the number of wash cycles before pumping an apparatus cleaning agent and shuts down if said means to sense a user's hand senses a user's hand close proximity to the cleansing apparatus.

5. The cleansing apparatus of claim 3 wherein said controller further comprises means to start said cleansing apparatus when said means to sense a user's hand senses a user's hand in close proximity to the cleansing apparatus.

6. The cleansing apparatus of claim 3 wherein said means to sense a user's hand in close proximity to the cleansing apparatus further comprises a photoeye.

7. The cleansing apparatus of claim 3 wherein said means to sense a user's hand in close proximity to the cleansing apparatus further comprises an ultrasonic sensor.

8. The cleansing apparatus of claim 3 wherein said means to sense a user's hand in close proximity to the cleansing apparatus further comprises a proximity sensor.

9. The cleansing apparatus of claim 1 wherein said opposite end of said open end of said cylinder further comprises fingertip cleansing nozzles, a drain, and a particle barrier in front of the drain.

10. The cleansing apparatus of claim 1 wherein said opposite end of said open end of said cylinder further comprises a drain basin having a float switch communicating with said controller to shut off the cleansing apparatus at a preset fluid height.

11. The cleansing system of claim 1 further comprising a leg operated switch to activate said programmable controller.

12. The cleansing system of claim 1 wherein said cleansing fluid further comprises 0.001–0.0052% CHG by volume with water.

13. The cleansing system of claim 1 wherein said means for conveying cleansing fluid to said nozzle means further comprises a shuttle valve allowing the use of three different cleansing fluids programmably selected by said programmable controller.

* * * * *